(12) United States Patent
Mohan Rao et al.

(10) Patent No.: US 7,429,661 B2
(45) Date of Patent: *Sep. 30, 2008

(54) INTERMEDIATES FOR LINEZOLID AND RELATED COMPOUNDS

(75) Inventors: Dodda Mohan Rao, Hyderabad (IN); Pingili Krishna Reddy, Hyderabad (IN)

(73) Assignee: Symed Labs Limited (IN)

( * ) Notice: Subject to any disclaimer, the term of this patent is extended or adjusted under 35 U.S.C. 154(b) by 298 days.

This patent is subject to a terminal disclaimer.

(21) Appl. No.: 10/524,623

(22) PCT Filed: Jul. 20, 2004

(86) PCT No.: PCT/IN2004/000218

§ 371 (c)(1), (2), (4) Date: Jan. 26, 2006

(87) PCT Pub. No.: WO2006/008754

PCT Pub. Date: Jan. 26, 2006

(65) Prior Publication Data

US 2006/0247435 A1 Nov. 2, 2006

(51) Int. Cl.
*C07D 413/12* (2006.01)
*C07D 209/48* (2006.01)

(52) U.S. Cl. ................................ 544/144; 548/465
(58) Field of Classification Search .............. 544/137, 544/144; 548/465
See application file for complete search history.

(56) References Cited

U.S. PATENT DOCUMENTS 5,688,792 A   11/1997  Barbachyn et al.
5,837,870 A   11/1998  Pearlman et al.
7,034,017 B2 *  4/2006  Straub et al. ............. 514/230.8
7,307,163 B2 * 12/2007  Mohan Rao et al. ........ 544/137

FOREIGN PATENT DOCUMENTS

| EP | 4024 A2 | 9/1979 |
| EP | 50827 A1 | 5/1982 |
| EP | 0275742 A1 | 7/1988 |
| FR | 2506769 A | 12/1982 |
| WO | WO 95/07271 A1 | 3/1995 |
| WO | WO 99/24393 A1 | 5/1999 |

OTHER PUBLICATIONS

J. Med Chem, 39(3), 673-679 (1996).
Tetrahedron Lett., 40(26), 4855, 1999.
International Search Report dated Jul. 20, 2004.
Abstract of CN 1355165A.

* cited by examiner

*Primary Examiner*—Joseph McKane
*Assistant Examiner*—Jason M Nolan
(74) *Attorney, Agent, or Firm*—Caesar, Rivise, Bernstein, Cohen & Pokotilow, Ltd.

(57) ABSTRACT

The present invention provides a novel process for preparation of 5 aminomethyl substituted oxazolidinones, key intermediates for oxazolidinone antibacterials including linezolid. Thus, the key intermediate of linezolid is prepared by a) reacting N-[3-Chloro-2-(R)-hydroxypropyl]-3-fluoro-4-morpholinyl aniline with potassium phthalimide; b) subjecting N-[3-pthalimido-2-(R)-hydroxypropyl]-3-fluoro-4-(morpholinyl) aniline produced in the above step to carbonylation; and c) reacting (S)-N-[[3-[3-Fluoro-4-[4-morpholinyl]phenyl]-2-oxo-5-oxazolidiriyl]methyl]phthalimide produced in the above step with hydrazine hydrate to produce (S)-N-[[3-[3-Fluoro-4-[4-morpholinyl]phenyl]-2-oxo-5-oxazolidinyl]methyl]amine.

66 Claims, No Drawings

INTERMEDIATES FOR LINEZOLID AND RELATED COMPOUNDS

FIELD OF THE INVENTION

The present invention provides novel processes for preparation of 5-aminomethyl substituted oxazolidinones, key intermediates for oxazolidinone antibacterials.

BACKGROUND OF THE INVENTION

U.S. Pat. No. 5,688,792 (U.S. Pat. No. 5,688,792) disclosed oxazine and thiazine oxazolidinone derivatives. The compounds are antimicrobial agents. Among them linezolid, chemically N-[[(5S)-3-[3-fluoro-4-(4-morpholinyl)phenyl]-2-oxo-5-oxazolidinyl]methyl]acetamide is the most important antibacterial agent. Linezolid is represented by the following structure:

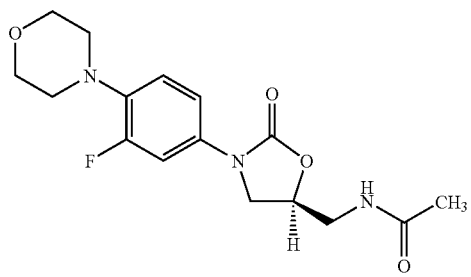

Processes for preparation of linezolid were described in U.S. Pat. No. 5,837,870, WO 99/24393, WO 95/07271, J. Med. Chem. 39(3), 673-679, 1996 and Tetrahedron Lett., 40(26), 4855, 1999.

According to prior art processes, the 5-hydroxymethyl substituted oxazolidinones are converted to the corresponding 5-aminomethyl substituted oxazolidinones, key intermediates in the production of oxazolidinone antibacterial pharmaceuticals.

The prior art processes for preparing 5-aminomethyl substituted oxazolidinones are associated with many drawbacks. For instant in the preparation of linezolid, WO 95/07271 uses butyl lithium at very low temperature (−78° C.). It is known that the handling of butyl lithium is difficult and the person skilled in the art appreciate a process that produces the product in good yield avoiding the 'difficult to handle' reagents.

We have discovered novel intermediates useful for preparing oxazolidinone antibacterials. The novel intermediates can be prepared in high yields using easy to handle reagents. The novel intermediates can be converted to oxazolidinone antibacterials using common reagents, also in good yields.

SUMMARY OF INVENTION

The present invention provides a novel process to prepare 5-aminomethyl substituted oxazolidinones of formula I:

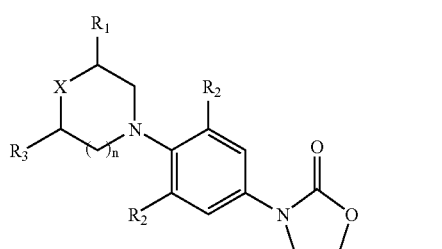

wherein
X is O, S, SO or $SO_2$;
$R_1$ is H, $CH_3$ or CN;
$R_2$ is independently H, F or Cl;
$R_3$ is H or $CH_3$;
n is 0, 1 or 2;
which comprises;

a) (i) reacting the compound of formula II:

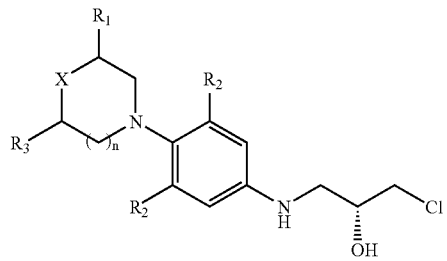

wherein $R_1$, $R_3$, X, $R_2$ and n are as defined in formula I;
with potassium phthalimide of formula III:

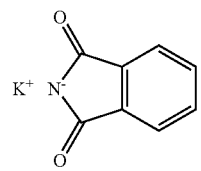

to produce compounds of formula IV:

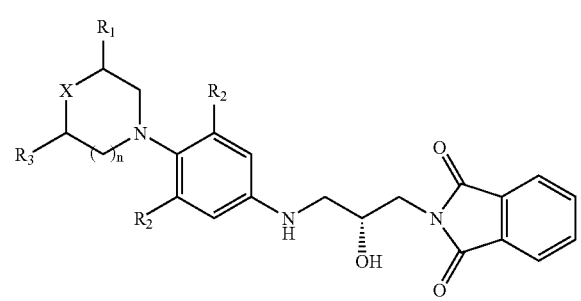

wherein $R_1$, $R_3$, X, $R_2$ and n are as defined in formula I;
(or)
(ii) reacting the compound of formula V:

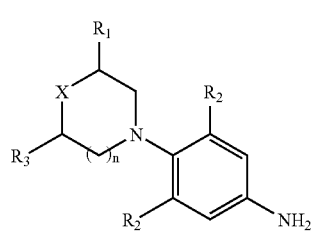

wherein R₁, R₃, X, R₂ and n are as defined in formula I;
with phthalimido oxiranyl compound of formula VI:

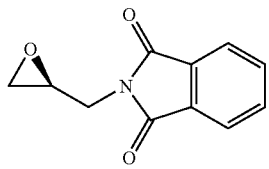

VI b) converting the product of step (a) to produce a compound of formula VII:

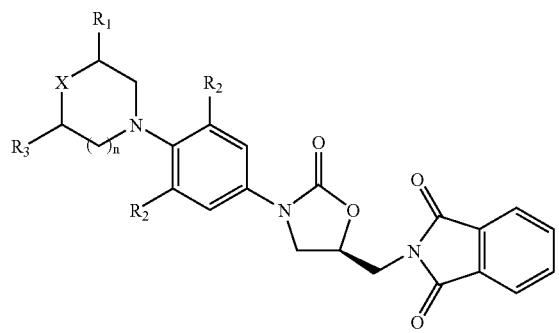

VII and c) converting the product of step (b) to aminomethyl oxazolidinone of formula I.

The compounds of formula IV are novel and provides another aspect of the present invention.

DETAILED DESCRIPTION OF THE INVENTION

The present invention provides a novel process for preparing 5-aminomethyl substituted oxazolidinones of formula I:

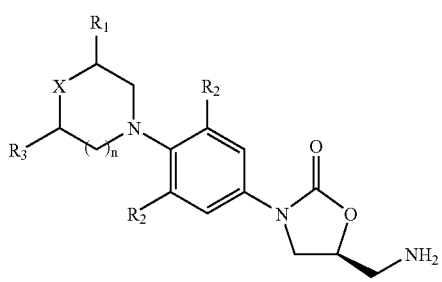

I wherein
X is O, S, SO or SO₂;
R₁ is H, CH₃ or CN;
R₂ is independently H, F or Cl;
R₃ is H or CH₃;
n is 0, 1 or 2.

The compounds of formula I are key intermediates for preparing known oxazolidinone antibacterials.

Step-a) The chlorohydrin compound of formula II:

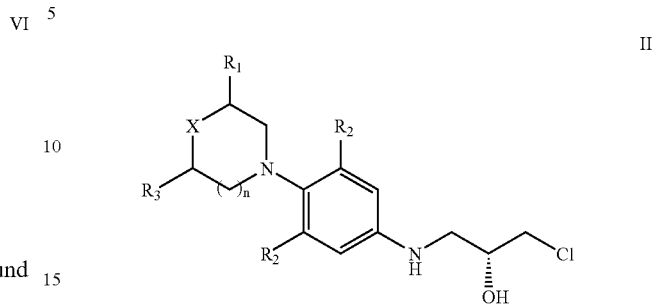

II wherein R₁, R₃, X, R₂ and n are as defined in formula I; is reacted with potassium phthalimide of formula III:

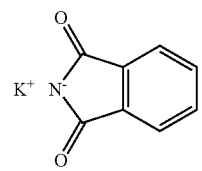

III to provide phthalimido compound of formula IV:

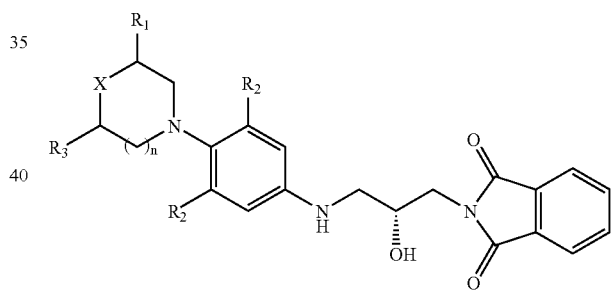

IV wherein R₁, R₃, X, R₂ and n are as defined In formula I.

The reaction is carried out by contacting the chlorohydrin compounds with potassium phthalimide in a solvent or mixture of solvents. Selection of solvent is not critical, but preferable solvents are those that dissolve both the chlorohydrin compounds and potassium phthalimide to ensure maximum contact between the reactants resulting in faster reaction. However, the process is also operable with solvents that only partially dissolve the chlorohydrin compounds or potassium phthalimide. The preferable solvent is dimethylformamide or acetonitrile.

The reaction is performed preferably between about 10° C. and the boiling temperature of the solvent used, more preferably between 40° C. and the boiling temperature of the solvent and most preferably at the boiling temperature of the solvent used.

Time required for completion of the reaction depends on factors such as solvent used and temperature at which the reaction is carried out. For example, if the reaction is carried out by contacting the chlorohydrin compounds with potassium phthalimide in dimethylformamide under reflux conditions, about 2 to 10 hours is required for the reaction completion.

Alternatively the compound of formula IV is prepared by reacting the compound of formula V:

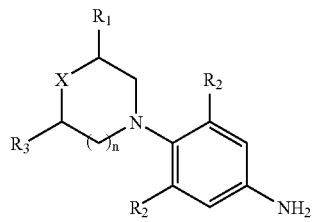

wherein $R_1$, $R_3$, X, $R_2$ and n are as defined in formula I; with phthalimido oxiranyl compound of formula VI:

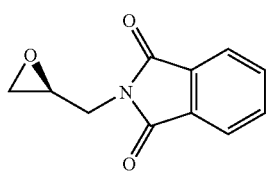

The quantity of phthalimido oxiranyl compound is not critical, but for better yield at least one molar equivalent is required per equivalent of phenyl amine of formula V.

The reaction between the compounds of formula V and formula VI is carried out in a solvent. Any solvent, which is neutral towards the reactants, may be used. Operable solvents include cyclic ethers such as tetrahydrofuran; amides such as N,N-dimethylformamide and N,N-dimethylacetamide; acetonitrile; and alcohols such as methanol, ethanol, t-amyl alcohol, t-butyl alcohol and Isopropyl alcohol; and a mixture thereof. Preferable solvent is selected from methanol, Isopropyl alcohol and N,N-dimethylformamide.

The reaction is performed at or below boiling temperature of the solvent used, more preferably between 10° C. and boiling temperature of the solvent used and even more preferably at boiling temperature of the solvent used.

Time required for completion of the reaction depends on factors such as solvent used and temperature at which the reaction is carried.

The product obtained may be used directly in the next step, or it can be isolated from the reaction mixture and used in the next step.

Step (b) The phthalimido compound of formula IV produced as above is subjected to cabonylation to provide phthalimido oxazolidinone compound of formula VII.

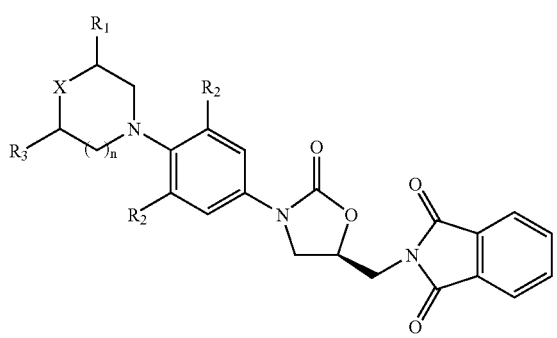

The carbonylation is performed using any carbonylating reagent commonly known for such purpose. Among them carbonyldiimidazole, phosgene, diethyl carbonate, triphosgene, alkyl chloroformates such as ethyl chloroformate, aryl chloroformates such as phenyl chloroformate and aralkyl chloroformates such as benzyl chloroformate are preferred; carbonyldiimidazole, diethyl carbonate and triphosgene are being more preferred.

The carbonylation reaction is preferably performed by contacting the phthalimido compound of formula IV with carbonylating agent in the presence of an aprotic solvent or a mixture thereof. More preferably the phthalimido compound of formula IV is reacted with at least one molar equivalent of the carbonylating agent in the presence of an aprotic solvent such as methylene dichloride, ethylenedichloride or chloroform.

The phthalimido compounds of formula VII are known and can be converted to the aminomethyl oxazolidinone compounds by using for example Hydrazine hydrate or aqueous methylamine. These methods are known and are described in U.S. Pat. No. 5,688,792.

The aminomethyl oxazolidinone compounds of formula I are acylated by known methods using acylating agents such as acyl halides or acyl anhydrides to form the corresponding 5-acylaminomethyloxazolidinone compounds of formula VIII:

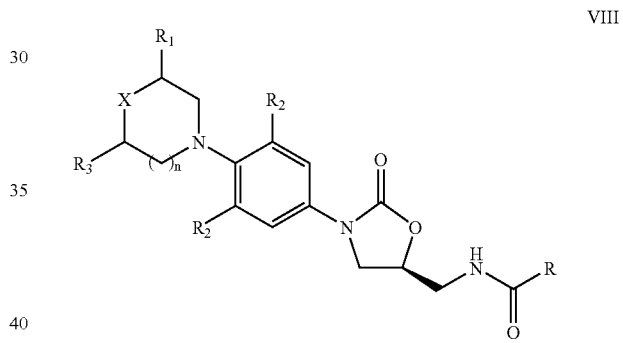

wherein $R_1$, $R_3$, X, $R_2$ and n are as defined in formula I; R represents $C_1$ to $C_8$ straight or branched alkyl groups. The preferred alkyl group is $CH_3$.

The acylation can be carried out by known methods such as those described in U.S. Pat. No. 5,688,792.

One compound of formula VIII can be converted to another compound of formula VII. Thus for example compounds of formula VIII, wherein X is S can be converted to the compounds of formula VIII, wherein X is SO or $SO_2$ by the methods such as those disclosed in U.S. Pat. No. 5,688,792.

The 5-acyl amino methyl substituted oxazolidinone of formula VIII are known to be antibacterial pharmaceutical agents.

The compounds of formula II and VI have the right configuration to obtain the compounds of formula I and VII. The configurations of formula II and VI are retained through out the sequence of reactions of the invention. However, it is readily apparent to one skilled in the art that one could easily perform the identical process steps with the opposite enantiomeric form or racemic form to obtain the corresponding stereo isomers.

Therefore, using the chemistry of the claimed process with any of the enantiomeric forms is considered equivalent to the claimed processes.

The compounds of formula II used as starting materials can be obtained by the process described in our co-pending international application No. PCT/IN04/00105. Thus, the compound of formula II is prepared by reacting a compound of formula V:

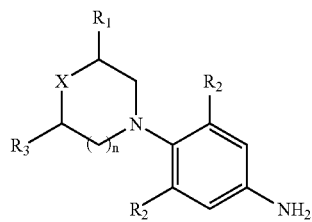

wherein $R_1$, $R_3$, X, $R_2$ and n are as defined in formula I; with (R)-epichlorohydrin of formula IX:

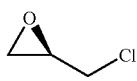

Phthalimido oxiranyl compound VI used as starting material is commercially available.

In particular most important compound of formula VIII is linezolid (VIII, $R_1$ and $R_3$ is H; X is O, one $R_2$ is H and the other $R_2$ is F; n is 1).

The most preferred process for preparing linezolid is described as under:

a) N-[3-Chloro-2-(R)-hydroxypropyl]-3-fluoro-4-morpholinyl aniline is reacted with potassium phthalimide to provide N-[3-pthalimido-2-(R)-hydroxypropyl]-3-fluoro-4-(morpholinyl)aniline (Formula IV, $R_1$=$R_3$ is H; X is O; one $R_2$ is H and the other $R_2$ is F; and n is 1).

The reaction is carried out by contacting the N-[3-Chloro-2-(R)-hydroxypropyl]-3-fluoro-4-morpholinylaniline, with potassium phthalimide in a solvent or a mixture of solvents. Selection of solvent is not critical, but preferable solvents are those that dissolve both the chlorohydrin compounds and potassium phthalimide to ensure maximum contact between the reactants resulting in faster reaction. However, the process is also operable with solvents that only partially dissolve the chlorohydrin compounds or potassium phthalimide. The preferable solvent is dimethylformamide or acetonitrile.

The reaction is performed preferably between about 10° C. and the boiling temperature of the solvent used, more preferably between 40° C. and the boiling temperature of the solvent, and most preferably at the boiling temperature of the solvent used.

Time required for completion of the reaction depends on factors such as solvent used and temperature at which the reaction is carried out. For example, if the reaction is carried out by contacting the chlorohydrin compounds with potassium phthalimide in dimethylformamide under reflux conditions, about 3 to 7 hours is required for the reaction completion.

Alternatively 3-fluoro-4-morpholinyl aniline (formula V, $R_1$=$R_3$ is H; X is O; one $R_2$ is H and the other $R_2$ is F; and n is 1) is reacted with phthalimido oxiranyl compound of formula VI to provide. N-[3-pthalimido-2-(R)-hydroxypropyl]-3-fluoro-4-(morpholinyl)aniline (Formula IV, $R_1$=$R_3$ is H; X is O; one $R_2$ is H and the other $R_2$ is F; and n is 1).

The quantity of phthalimido oxiranyl compound is not critical, but for better yield at least one molar equivalent is required per equivalent of 3-fluoro-4-morpholinyl aniline.

Any solvent, which is neutral towards the reactants, may be used. Operable solvents include cyclic ethers such as tetrahydrofuran; amides such as N,N-dimethylformamide and N,N-dimethylacetamide; acetonitrile; and alcohols such as methanol, ethanol, t-amyl alcohol, t-butyl alcohol and Isopropyl alcohol. Preferable solvent is selected from methanol, isopropyl alcohol and N,N-dimethylformamide.

The reaction is performed at or below boiling temperature of the solvent used, more preferably between 10° C. and boiling temperature of the solvent used and even more preferably at boiling temperature of the solvent used.

The product obtained can be used directly in the next step, or it can be isolated from the reaction mixture and used in the next step.

b) N-[3-pthalimido-2-(R)-hydroxypropyl]-3-fluoro-4-(morpholinyl)aniline produced as above is subjected to carbonylation to provide (S)-N-[3-[3-Fluoro-4-[4-morpholinyl]phenyl]-2-oxo-5-oxazolidinyl]methyl]phthalimide (Formula VII, $R_1$=$R_3$ is H; X is O; one $R_2$ is H and the other $R_2$ is F; and n is 1).

The carbonylation is performed using any carbonylating reagent commonly known for such purpose. Among them carbonyldiimidazole, phosgene, methyl chloroformate, benzyl chloroformate, diethyl carbonate, triphosgene and phenylchloroformate are preferred; carbonyldiimidazole, diethyl carbonate and triphosgene are being more preferred.

The carbonylation reaction is preferably performed by contacting the N-[3-phthalimido-2-(R)-hydroxypropyl]-3-fluoro-4-morpholinylaniline with carbonylating agent in the presence of an aprotic solvent or a mixture of aprotic solvents. More preferably the N-[3-phthalimido-2-(R)-hydroxypropyl]-3-fluoro-4-morpholinylaniline is reacted with at least one molar equivalent of the carbonylating agent in the presence of an aprotic solvent such as methylene dichloride, ethylenedichloride or chloroform.

c) (S)-N-[[3-[3-Fluoro-4-[4-morpholinyl]phenyl]-2-oxo-5-oxazolidinyl]methyl]phthalimide produced as above is reacted with hydrazine hydrate or aqueous methyl amine to produce S—N-[[3-[3-Fluoro-4-[4-morpholinyl]phenyl]-2-oxo-5-oxazolidinyl]methyl]amine (Formula I, $R_1$=$R_3$ is H; X is O; one $R_2$ is H and the other $R_2$ is F; and n is 1). These methods of deprotection are known and described for example in U.S. Pat. No. 5,688,792.

d) S—N-[[3-[3-Fluoro-4-[4-morpholinyl]phenyl]-2-oxo-5-oxazolidinyl]methyl]amine is reacted with acetic anhydride to produce linezolid.

The following examples are given for the purpose of illustrating the present invention and should not be considered as limitations on the scope and spirit of the invention.

EXAMPLES

Example 1

3-Fluoro-4-morpholinyl aniline (39 gm) is mixed with (R)-epichlorohydrin (18.5 gm) and isopropyl alcohol (200 ml) and heated to reflux for 16 hours. The solvent is distilled off to give 57 gm residue of N-[3-Chloro-2-(R)-hydroxypropyl]-3-fluoro-4-morpholinyl aniline.

Example 2

The mixture of (N-[3-Chloro-2-(R)-hydroxypropyl]-3-fluoro-4-morpholinyl aniline obtained in example 1, potassium phthalimide (40 gm) and Dimethyl formamide (400 ml) is heated for 5 hours at reflux temperature. The reaction mixture is cooled to ambient temperature, poured in to water (2 L) and filtered the solid obtained, and recrystallized from isopropyl alcohol to give 50 gm N-[3-pthalimido-2-(R)-hydroxypropyl]-3-fluoro-4-(morpholinyl)aniline.

Example 3

3-Fluoro-morpholinyl aniline (39 gm) is mixed with (S)-N-2,3-epoxypropylphthalimide (40 gm) and dimethylformamide (400 ml) and heated to reflux for 5 hours. The reaction mixture is cooled to ambient temperature, poured into 2 liter water and filtered the solid obtained to give 60 gm of N-[3-pthalimido-2-(R)-hydroxypropyl]-3-fluoro-4-(morpholinyl) aniline.

Example 4

N-[3-pthalimido-2-(R)-hydroxypropyl]-3-fluoro-4-(morpholinyl)aniline (57 gm) is dissolved in methylene dichloride (600 ml), carbonyl diimidazole (32 gm) is added at ambient temperature and the reaction mixture is stirred for 20 hours. The reaction mass is washed with water and methylene dichloride is distilled to give 48 gm of (S)-N-[[3-[3-Fluoro-4-[4-morpholinyl]phenyl]-2-oxo-5-oxazolidinyl]methyl]phthalimide as solid.

Example 5

Methanol (240 ml) and Hydrazine hydrate (26 gm) are added to a flask containing the (S)-N-[[3-[3-Fluoro-4-[4-morpholinyl]phenyl]-2-oxo-5-oxazolidinyl]methyl]phthalimide (40 gm), heated for 1 hour at reflux temperature and cooled to ambient temperature, water (500 ml) is added to the reaction mass and extracted with methylene dichloride (300 ml). The combined extractions are washed with water (100 ml) and the solvent is distilled to give 20 gm of S—N-[[3-[3-Fluoro-4-[4-morpholinyl]phenyl]-2-oxo-5-oxazolidinyl]methyl]anine.

Example 6

S—N-[[3-[3-Fluoro-4-[4-morpholinyl]phenyl]-2-oxo-5-oxazolidinyl]methyl]amine (20 gm) is stirred in toluene (200 ml) for 15 minutes, acetic anhydride (20 gm) is added drop wise at ambient temperature and stirred for 1 hour. The reaction mixture is cooled to 0-5° C., filtered the solid and recrystallized from methanol (200 ml) to give 16 gm of N-[[(5S)-3-[3-fluoro-4-(4-morpholinyl)phenyl]-2-oxo-5-oxazolidinyl]methyl]acetamide.

We claim:
1. A process for the preparation of 5-aminomethyl substituted oxazolidinones of formula I:

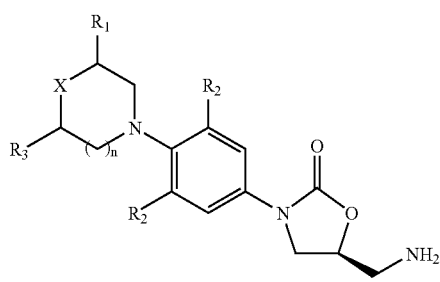

wherein
X is O, S, SO or $SO_2$;
$R_1$ is H, $CH_3$ or CN;
$R_2$ is independently H, F or Cl;
$R_3$ is H or $CH_3$;
n is 0, 1 or 2;
which comprises;
a) (i) reacting the compound of formula II:

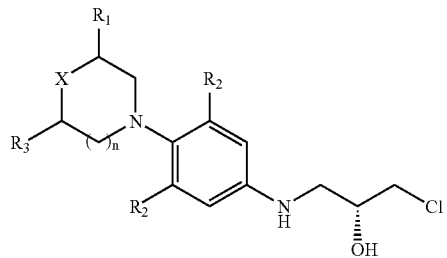

wherein $R_1$, $R_3$, X, $R_2$ and n are as defined in formula I; with potassium phthalimide of formula III:

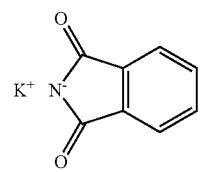

to produce compounds of formula IV:

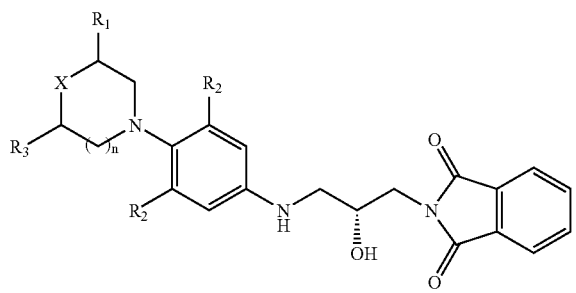

wherein $R_1$, $R_3$, X, $R_2$ and n are as defined in formula I; (or)
ii) reacting the compound of formula V:

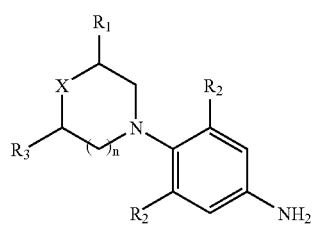

wherein $R_1$, $R_3$, X, $R_2$ and n are as defined in formula I; with phthalimido oxiranyl compound of formula VI:

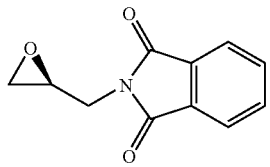

b) converting the product of step (a) to produce a compound of formula VII:

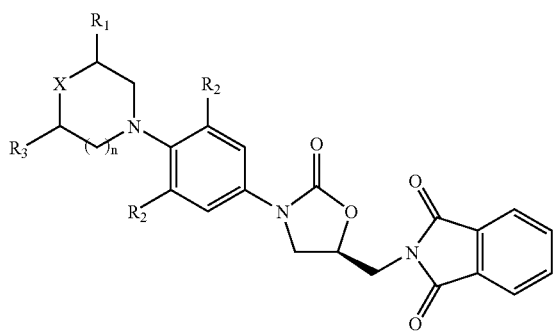

and c) converting the product of step (b) to aminomethyl oxazolidinone of formula I.

2. The process according to claim 1, wherein the aminomethyl oxazolidinone formed is the compound of formula I, wherein $R_1=R_3$ is H; $R_2$ is independently H and F; X is O or S; and n is 1.

3. The process according to claim 2, wherein the aminomethyl oxazolidinone is the compound of formula I, wherein X is O.

4. The process according to claim 2, wherein the aminomethyl oxazolidinone is the compound of formula I, wherein one $R_2$ is H and the other $R_2$ is F; X is O.

5. The process according to claim 1, wherein the reaction in step (a)(i) is carried out by contacting the chlorohydrin compounds of formula II with potassium phthalimide in a solvent or mixture of solvents.

6. The process according to claim 5, wherein the solvent is dimethyl formamide or acetonitrile.

7. The process according to claim 5, wherein the reaction is carried out between about 10° C. and the boiling temperature of the solvent used.

8. The process according to claim 7, wherein the reaction is carried out between about 40° C. and the boiling temperature of the solvent used.

9. The process according to claim 8, wherein the reaction is carried out at boiling temperature of the solvent used.

10. The process according to claim 1, wherein the quantity of phthalimido oxiranyl compound in step (a)(ii) is at least one molar equivalent per equivalent of phenyl amine of formula V.

11. The process according to claim 1, wherein the reaction between the compounds of formula V and formula VI in step (a)(ii) is carried out in a solvent.

12. The process according to claim 11, wherein the solvent is neutral towards the reactants.

13. The process according to claim 12, wherein the solvent is selected from cyclic ethers, amides, acetonitrile and alcohols; and a mixture thereof.

14. The process according to claim 13, wherein the solvent is selected from tetrahydrofuran, N,N-dimethylformamide, N,N-dimethylacetamide, acetonitrile, methanol, ethanol, t-amyl alcohol, t-butyl alcohol and isopropyl alcohol.

15. The process according to claim 14, wherein the solvent is selected from methanol, isopropyl alcohol and N,N-dimethylformamide.

16. The process according to claim 15, wherein the solvent is methanol.

17. The process according to claim 15, wherein the solvent is isopropyl alcohol.

18. The process according to claim 15, wherein the solvent is N,N-dimethylformamide.

19. The process according to claim 1, wherein the reaction in step (a)(ii) is performed at or below boiling temperature of the solvent used.

20. The process according to claim 19, wherein the reaction is performed between about 10° C. and boiling temperature of the solvent used.

21. The process according to claim 20, reaction is performed at the boiling temperature of the solvent used.

22. A process according to claim 1, wherein the phthalimido compound of formula IV is subjected in the step (b) to carbonylation using carbonylating reagent to provide phthalimido oxazolidinone compound of formula VII.

23. The process according to claim 22, wherein the carbonylating reagent is selected from carbonyldiimidazole, phosgene, alkyl chloroformates, aryl chloroformates, aralkyl chloroformates diethyl carbonate and triphosgene.

24. The process according to claim 23, wherein the alkyl chloroformate is methyl chloroformate, aryl chloroformate is phenyl chloroformate and aralkyl chloroformate is benzyl chloroformate.

25. The process according to claim 23, wherein the carbonylating reagent is carbonyldiimidazole or triphosgene or diethyl carbonate.

26. The process according to claim 25, wherein the carbonylating reagent is carbonyldiimidazole.

27. The process according to claim 25, wherein the carbonylating reagent is diethyl carbonate.

28. The process according to claim 25, wherein the carbonylating reagent is triphosgene.

29. The process according to claim 22, wherein the carbonylation reaction is performed in the presence of an aprotic solvent or a mixture thereof.

30. The process according to claim 29, wherein the aprotic solvent is selected from methylenedichloride, ethylenedichloride and chloroform.

31. The process according to claim 30, wherein the aprotic solvent is methylenedichloride.

32. The process according to claim 30, wherein the aprotic solvent is chloroform.

33. The process according to claim 1, wherein the phthalimido oxazolidinone compound of formula VII is converted in the step (c) to the compound of formula I as defined in claim 1, which comprises reacting the said phthalimido oxazolidinone with hydrazine hydrate to obtain the said compound of formula I.

34. A process for the preparation of linezolid intermediate of formula:

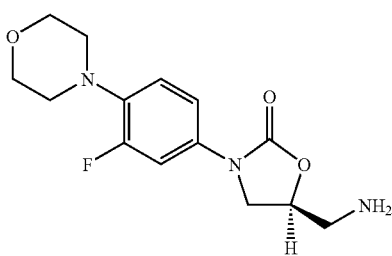

which comprises:
a) (i) reacting N-[3-Chloro-2-(R)-hydroxypropyl]-3-fluoro-4-morpholinyl aniline with potassium phthalimide to produce N-[3-pthalimido-2-(R)-hydroxypropyl]-3-fluoro-4-(morpholinyl)aniline;
(or)
(ii) reacting 3-fluoro-4-morpholinyl aniline with (S)-N-2,3-epoxypropyl phthalimide to produce N-[3-pthalimido-2-(R)-hydroxypropyl]-3-fluoro-4-(morpholinyl) aniline;
b) subjecting N-[3-pthalimido-2-(R)-hydroxypropyl]-3-fluoro-4-(morpholinyl) aniline produced in step (a) to carbonylation using a carbonylating agent to produce (S)-N-[3-[3-Fluoro-4-[4-morpholinyl]phenyl]-2-oxo-5-oxazolidinyl]methyl]phthalimide; and
c) reacting (S)-N-[[3-[3-Fluoro-4-[4-morpholinyl]phenyl]-2-oxo-5-oxazolidinyl]methyl]phthalimide produced in step (b) with hydrazine hydrate or aqueous methyl amine to produce S-N-[[3-[3-Fluoro-4-[4-morpholinyl]phenyl]-2-oxo-5-oxazolidinyl]methyl]amine.

35. The process according to claim 34, further characterized by reacting S-N-[[3-[3-Fluoro-4-[4-morpholinyl]phenyl]-2-oxo-5-oxazolidinyl]methyl]amine produced in step (c) with acetic anhydride to produce linezolid of formula:

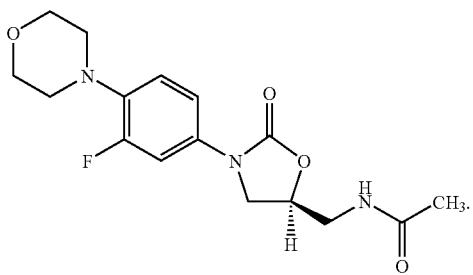

36. The process according to claim 34, wherein the reaction in step (a) (i) is carried out in a solvent or a mixture thereof.

37. The process according to claim 36, wherein the solvent is dimethylformamide or acetonitrile.

38. The process according to claim 34, wherein the reaction in the step (a) (i) is performed between about 10° C. and the boiling temperature of the solvent used.

39. The process according to claim 38, wherein the reaction is performed between about 40° C. and boiling temperature.

40. The process according to claim 39, wherein the reaction is performed at boiling temperature of the solvent used.

41. The process according to claim 34, wherein the reaction in step (a) (ii) is carried out in a solvent or a mixture thereof.

42. The process according to claim 41, wherein the solvent is selected from cyclic ethers, amides, acetonitrile and alcohols; or a mixture thereof.

43. The process according to claim 42, wherein the solvent is selected from tetrahydrofuran, N,N-dimethylformamide, N,N-dimethylacetamide, acetonitrile, methanol, ethanol, t-amyl alcohol, t-butyl alcohol and isopropyl alcohol.

44. The process according to claim 43, wherein the solvent is selected from methanol, isopropyl alcohol and N,N-dimethylformamide.

45. The process according to claim 44, wherein the solvent is methanol.

46. The process according to claim 44, wherein the solvent is isopropyl alcohol.

47. The process according to claim 44, wherein the solvent is N,N-dimethylformamide.

48. The process according to claim 34, wherein the reaction in step (a) (ii) is performed at or below boiling temperature of the solvent used.

49. The process according to claim 48, wherein the reaction is performed between about 10° C. and boiling temperature of the solvent used.

50. The process according to claim 49, reaction is performed at the boiling temperature of the solvent used.

51. The process according to claim 34, wherein the carbonylating reagent in step (b) is selected from carbonyldiimidazole, phosgene, diethyl carbonate, triphosgene, alkyl chloroformate, aryl chloroformate and aralkyl chloroformate.

52. The process according to claim 51, wherein the alkyl chloroformate is methyl chloroformate, aryl chloroformate is phenyl chloroformate and aralkyl chloroformate is benzyl chloroformate.

53. The process according to claim 51, wherein the carbonylating reagent is carbonyldiimidazole or triphosgene or diethyl carbonate.

54. The process according to claim 53, wherein the carbonylating reagent is carbonyldiimidazole.

55. The process according to claim 53, wherein the carbonylating reagent is diethyl carbonate.

56. The process according to claim 53, wherein the carbonylating reagent is triphosgene.

57. The process according to claim 34, wherein the carbonylation reaction in the step (b) is performed in the presence of an aprotic solvent or a mixture thereof.

58. The process according to claim 57, wherein the aprotic solvent is selected from methylenedichloride, ethylenedichloride and chloroform.

59. The process according to claim 58, wherein the aprotic solvent is methylenedichloride.

60. The process according to claim 58, wherein the aprotic solvent is chloroform.

61. The process according to claim 34, wherein the step (c), the reaction is carried out in a solvent.

62. The process according to claim 61, wherein the solvent is selected from methanol, ethanol and isopropyl alcohol.

63. The process according to claim 35, wherein the reaction is carried out in toluene or acetone.

64. A compound of formula IV:
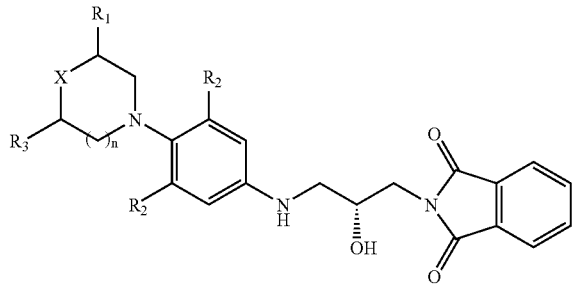
wherein
X is O, S, SO or SO$_2$;
R$_1$ is H, CH$_3$ or CN;
R$_2$ is independently H, F or Cl;
R$_3$ is H or CH$_3$;
n is 0, 1 or 2.
65. The compound of formula IV as defined in claim 64, wherein R$_1$=R$_3$ is H; R$_2$ is independently H and F; X is O or S; and n is 1.
66. The compound of formula IV as defined in claim 65, wherein one R$_2$ is H and the other R$_2$ is F; and X is O.
* * * * *